US009084039B2

(12) United States Patent
Schumacher et al.

(10) Patent No.: US 9,084,039 B2
(45) Date of Patent: Jul. 14, 2015

(54) OVERLOAD PROTECTION FOR LOUDSPEAKERS IN EXHAUST SYSTEMS

(71) Applicant: J. Eberspächer GmbH & Co. KG, Esslingen (DE)

(72) Inventors: Uwe Schumacher, Soest (DE); Christof Luecking, Wetter (DE); Manfred Nicolai, Esslingen (DE)

(73) Assignee: Eberspächer Exhaust Technology GmbH & Co., Esslingen (DE)

(*) Notice: Subject to any disclaimer, the term of this patent is extended or adjusted under 35 U.S.C. 154(b) by 435 days.

(21) Appl. No.: 13/666,296

(22) Filed: Nov. 1, 2012

(65) Prior Publication Data

US 2013/0108067 A1 May 2, 2013

(30) Foreign Application Priority Data

Nov. 2, 2011 (DE) ......................... 10 2011 117 495

(51) Int. Cl.
*A61F 11/06* (2006.01)
*H04R 3/00* (2006.01)
*G10K 11/178* (2006.01)

(52) U.S. Cl.
CPC .............. *H04R 3/007* (2013.01); *G10K 11/178* (2013.01); *G10K 2210/121* (2013.01)

(58) Field of Classification Search
None
See application file for complete search history.

(56) References Cited

U.S. PATENT DOCUMENTS 4,177,874 A 12/1979 Angelini et al.
5,097,923 A * 3/1992 Ziegler et al. ................. 181/206
5,229,556 A 7/1993 Geddes
5,233,137 A 8/1993 Geddes
5,336,856 A * 8/1994 Krider et al. .................. 181/206
5,343,533 A * 8/1994 Geddes ......................... 381/71.7

(Continued)

FOREIGN PATENT DOCUMENTS

DE 69 111 402 T2 1/1996
DE 197 51 596 A1 6/1999
DE 10 2006 042 224 B3 1/2008
DE 10 2007 030 250 A1 1/2009

(Continued)

OTHER PUBLICATIONS

Don D. Davis, Jr. George M. Stokes, Dewey Morre, George L. Stevens, Jr. National Advisroy committee for Aeronautics, Report 1192, Theoretical and Experimental Investigation of Mufflers with comments on engine-exhaust muffler design. Jan. 1, 1954. pp. 1-47.*

*Primary Examiner* — Duc Nguyen
*Assistant Examiner* — Assad Mohammed
(74) *Attorney, Agent, or Firm* — McGlew and Tuttle, P.C.

(57) ABSTRACT

A method for controlling an anti-sound system includes measuring sound within an exhaust system of a vehicle, calculating a control signal based on the measured sound, calculating a thermal load to be expected of the at least one loudspeaker of the anti-sound system during operation with a control signal based on a mathematical model of a thermal behavior of the loudspeaker and/or a mechanical load to be expected of the at least one loudspeaker of the anti-sound system based on a mathematical model of a mechanical behavior the loudspeaker, comparing the calculated thermal and/or mechanical load with a specified maximum load, operating the loudspeaker with the control signal, if the calculated thermal and/or mechanical load is smaller than or equal to the maximum load, and changing the spectrum of the control signal, in order to receive a corrected control signal, if the calculated load is greater than the maximum load.

22 Claims, 6 Drawing Sheets

(56) References Cited

U.S. PATENT DOCUMENTS

| | | | | |
|---|---|---|---|---|
| 5,386,472 | A | 1/1995 | Pfaff et al. | |
| 5,432,857 | A | 7/1995 | Geddes | |
| 5,571,239 | A * | 11/1996 | Kameda et al. | 123/184.53 |
| 5,600,106 | A | 2/1997 | Langley | |
| 5,619,020 | A | 4/1997 | Jones et al. | |
| 5,703,337 | A | 12/1997 | Geisenberger | |
| 2002/0118841 | A1 * | 8/2002 | Button et al. | 381/55 |
| 2006/0037808 | A1 | 2/2006 | Krüger et al. | |
| 2008/0053747 | A1 | 3/2008 | Krüger et al. | |
| 2009/0173568 | A1 | 7/2009 | Kassner | |
| 2009/0255754 | A1 | 10/2009 | Krüger et al. | |
| 2011/0000734 | A1 | 1/2011 | Krüger et al. | |

FOREIGN PATENT DOCUMENTS

| | | | |
|---|---|---|---|
| DE | 10 2008 018 085 | A1 | 10/2009 |
| DE | 10 2009 031 848 | A1 | 1/2011 |
| EP | 0 373 188 | B1 | 12/1993 |
| EP | 0 674 097 | A1 | 9/1995 |
| EP | 0 755 045 | A2 | 1/1997 |
| EP | 0 916 817 | A2 | 5/1999 |
| EP | 1 055 804 | A1 | 11/2000 |
| EP | 1 462 777 | A1 | 9/2004 |
| EP | 1 627 996 | A1 | 2/2006 |
| JP | 06-012088 | A | 1/1994 |
| JP | 2001-189993 | A | 7/2001 |
| WO | 02/21879 | A2 | 3/2002 |

* cited by examiner

OVERLOAD PROTECTION FOR LOUDSPEAKERS IN EXHAUST SYSTEMS

CROSS REFERENCE TO RELATED APPLICATIONS

This application claims the benefit of priority under 35 U.S.C. §119 of Patent Application No. 10 2011 117 495.1, filed Nov. 2, 2011 in Germany, entitled "Überlastungsschutz für Lautsprecher in Abgasanlagen", the contents of which is hereby incorporated by reference in its entirety.

FIELD OF THE INVENTION

The invention relates to an overload protection for loudspeakers which are used in exhaust systems of vehicles driven by combustion engines for the active cancellation or influencing of sound waves.

BACKGROUND OF THE INVENTION

Irrespective of the combustion engine design (e.g. reciprocating engine, rotary piston engine or free-piston engine), noises are generated resulting from the consecutive working cycles (in particular intake and compression of a fuel/air mixture, power and exhaust of the combusted fuel/air mixture), on the one hand, these noises pass through the combustion engine as structure-borne sound and are then radiated as airborne sound from the outside of the combustion engine, on the other hand, these noises are passing as airborne sound together with the combusted fuel/air mixture through an exhaust system of the combustion engine.

These noises are frequently perceived as disadvantageous, on the one hand, legal provisions for noise abatement exist, which have to be complied with by the manufacturers of vehicles operated with combustion engines. These legal provisions normally specify a maximum permissible sound pressure during the operation of the vehicle. Manufacturers, on the other hand, try to make sure that the vehicles operated with combustion engines they produce have a characteristic noise emission, intended to match the image of the respective producer and to appeal to customers. With modern engines that have low volumetric displacement, this characteristic noise emission can frequently no longer be ensured by ordinary means.

The noises which are passing through the combustion engine as structure-borne sound can be attenuated easily and are there-fore no problem with respect to noise abatement, as a rule.

The noises passing through the exhaust system as airborne sound together with the combusted fuel/air mixture are reduced by mufflers positioned upstream of the rear opening of the exhaust system. These mufflers may be positioned down-stream of catalytic converters, if present. Such mufflers can operate according to the absorption principle and/or reflec-tion principle, for example. Both operating methods have the disadvantage that they require a comparatively large volume and create relatively high resistance against the combusted fuel/air mixture, which means that the overall efficiency of the vehicle drops, while the fuel consumption increases.

As an alternative or in addition to mufflers, so-called anti-sound systems are being developed for some time, which superimpose electroacoustically generated anti-sound on airborne sound generated in the combustion engine and passing through the exhaust system. Such systems are known, for example, from the documents U.S. Pat. Nos. 4,177,874, 5,229,556, 5,233,137, 5,343,533, 5,336,856, 5,432,857, 5,600,106, 5,619,020, EP 0 373 188, EP 0 674 097, EP 0 755 045, EP 0 916 817, EP 1 055 804, EP 1 627 996, DE 197 51 596, DE 10 2006 042 224, DE 10 2008 018 085 and DE 10 2009 031 848.

Such anti-sound systems normally utilize a so-called Filtered-x Least Mean Squares (FxLMS) algorithm, which endeavors to control an error signal down to zero. This error signal is measured by means of an error microphone. The error signal is endeavored to be controlled down to zero by the output of sound by means of at least one loudspeaker that is connected by a fluid connection with the exhaust system.

In order to accomplish a destructive interference of the sound waves of the airborne sound generated by the combustion engine and conducted in the exhaust system and the anti-sound generated from the loudspeaker, the sound waves originating from the loudspeaker must correspond to the sound waves generated by the combustion engine and conducted in the exhaust system in terms of amplitude and frequency. However, the sound waves originating from the loudspeaker must comprise a phase shift of 180° relative to the airborne sound generated by the combustion engine and conducted in the exhaust system. The anti-sound for each frequency band of the airborne sound conducted in the exhaust pipe is calculated separately by means of the FxLMS algorithm, by determining a suitable frequency and phase position of two sine wave oscillations that are shifted relative to one another by 90°, and by calculating the amplitudes for these sine wave oscillations. The purpose of anti-sound systems is that the sound cancellation is audible and measurable at least outside of the exhaust system, but also inside of it, if necessary. In this document, the term anti-sound is used to distinguish the sound generated by the loudspeaker from the airborne sound generated by the combustion engine and conducted in the exhaust system. When considered by itself, anti-sound involves normal airborne sound.

A respective anti-sound system is supplied by the company J. Eberspächer GmbH & Co. KG, Eberspächerstrasse 24, 73730 Esslingen, Germany.

It is a disadvantage with known anti-sound systems for exhaust systems that the continuous operation of the loudspeaker can produce a thermal overload of the loudspeaker and especially of an oscillator coil of the loudspeaker and/or a mechanical overload (of a diaphragm or spider, for example) of the loudspeaker.

To prevent a thermal overload of the oscillator coil of a loudspeaker, it is proposed in WO 02/21879 to calculate the expected heating up of the oscillator coil when a signal is provided to the loudspeaker by means of a mathematical model of the thermal behavior of the loudspeaker and in particular of the oscillator coil, and to reduce the amplitude of the signal provided to the loudspeaker if necessary such, that a specified temperature of the oscillator coil will not be exceeded.

The solution proposed from WO 02/21879, however, is not suitable for loudspeakers of anti-sound systems for exhaust systems. When the signal provided to the loudspeaker is reduced in its amplitude, it can no longer be ensured that the legal provisions with respect to the maximum permissible sound pressure for the operation of the vehicle can be complied with. Moreover WO 02/21879 does not consider any mechanical overload.

SUMMARY OF THE INVENTION

Embodiments of the present invention thus seek to provide an overload protection for loudspeakers of anti-sound systems for exhaust systems which effectively prevents thermal overloading of an oscillator coil of the loudspeakers and/or mechanical overloading (of a diaphragm or a spider, for example) of the loudspeakers and at the same time adequately ensures that a permissible sound pressure of the airborne sound conducted in the exhaust system is not exceeded.

Embodiments relate to a method to control an anti-sound system for an exhaust system of a vehicle operated by a combustion engine for generating an anti-airborne sound in the exhaust system based on measured sound in order to cancel at least partially or preferably completely both in value and phase the airborne sound generated by a combustion engine and conducted in the exhaust system, in the vicinity of the position at which the sound is measured in the exhaust system. This sound cancellation should be audible and measurable at least outside of the exhaust system, but preferably also within the exhaust system. In this context "in the vicinity of the position at which the sound is measured" means that the position at which the sound is at least partially canceled is at a distance downstream or upstream the exhaust gas flow from the position, at which the sound is measured, which is not more than ten times and particularly not more than five times and more particularly not more than double of the maximum diameter of the exhaust system at the position at which the sound is measured, along the exhaust gas flow. The method comprises the steps of measuring sound inside of the exhaust system and calculating a control signal based on the measured sound. The control signal can be determined in a way that it results in a complete or partial cancellation of the airborne sound, if a loudspeaker arranged in the exhaust system is operated with the control signal. The method moreover comprises the step of calculating a thermal load of the at least one loudspeaker (and especially the oscillator coil of the at least one loudspeaker) of the anti-sound system that is to be expected when the at least one loudspeaker (and especially the oscillator coil of the at least one loudspeaker) is operated with the control signal by means of a mathematical model of the loudspeaker and especially oscillator coil (and especially a mathematical model of a thermal behavior of the at least one loudspeaker (and especially of the oscillator coil of the at least one loudspeaker)) and/or a mechanical load of the at least one loudspeaker that is to be expected when the at least one loudspeaker (and especially a diaphragm or spider of the at least one loudspeaker, for example) of the anti-sound system is operated with the control signal based on a mathematical model of the loudspeaker (and especially a mathematical model of a mechanical behavior of the at least one loudspeaker (and especially of a diaphragm or spider of the at least one loudspeaker)). Thus, either one of the thermal load and the mechanical load is calculated, or both of the thermal load and the mechanical load are calculated. The respective mathematical model can exist in the form of a formula, characteristic curve, or a table, for example. For this purpose, the mathematical model can be designed with respect to the thermal load of the oscillator coil of the at least one loudspeaker such as is described in WO 02/21879, for example. Reference is made to the corresponding teaching of this document in its entirety. The method furthermore comprises a step of comparing the calculated thermal load and/or calculated mechanical load with a specified maximum load. One common maximum load value or separate maximum load values can be set for the thermal load and the mechanical load. The method furthermore comprises a step of operating the at least one loudspeaker with the control signal, should the calculated thermal load and/or calculated mechanical load be smaller than or equivalent to the respective maximum load. The method furthermore comprises steps of changing the spectrum of the control signal in order to obtain a corrected control signal, if the calculated thermal load and/or calculated mechanical load is greater than the respective maximum load and of operating the at least one loudspeaker with the corrected control signal. The reduction of the thermal load of the at least one loudspeaker and/or of the mechanical load of the at least one loudspeaker will thus not be achieved by a general decrease of the amplitude of the control signal across all frequencies, but rather by a change of the spectrum of the control signal. The amplitudes of the frequencies, which only contribute a small amount to the sound cancellation, can be set to zero, for example.

According to a first embodiment, the step of changing the spectrum of the control signal comprises sub-steps of comparing amplitudes of individual frequencies of the control signal with a threshold value, of setting the amplitudes of those frequencies of the control signal to zero, the amplitudes of which are smaller than or equal to the threshold value, in order to obtain a corrected control signal, and of calculating a thermal load of the at least one loudspeaker (and especially of an oscillator coil of the at least one loudspeaker) of the anti-sound system to be expected during operation with the corrected control signal by means of a mathematical model of the at least one loudspeaker and especially oscillator coil (and especially a mathematical model of a thermal behavior of the at least one loudspeaker (and especially of the oscillator coil of the at least one loudspeaker)) and/or a mechanical load of the at least one loudspeaker (and especially of a diaphragm or spider of the at least one loudspeaker) of the anti-sound system to be expected during operation with the corrected control signal by means of a mathematical model of the at least one loudspeaker (and especially a mathematical model of a mechanical behavior of the at least one loudspeaker (and especially of a diaphragm or spider of the at least one loudspeaker)). According to the first embodiment, the step of changing the spectrum of the control signal further comprises sub-steps of comparing the calculated thermal load and/or calculated mechanical load with the respective specified maximum load, of increasing the threshold value and repeating the above steps, if the calculated thermal load and/or calculated mechanical load is greater than the respective maximum load, and of operating the at least one loudspeaker with the corrected control signal, as soon as the calculated thermal load and/or calculated mechanical load is smaller or equal to the respective maximum load. Thus, in this embodiment the amplitudes of frequencies below the threshold value are set to zero. Thus, the spectrum of the control signal is changed to the extent that frequencies with small amplitudes are canceled.

However, the present invention is not limited to setting amplitudes of frequencies to zero in case the amplitudes are below the threshold value. For reasons of sound design, it can alternatively be useful to set frequencies with large amplitudes to zero and to leave frequencies with small amplitudes unchanged. In this case, the amplitudes of those frequencies of the control signal are set to zero, which amplitudes are higher than the threshold value, in order to obtain a corrected control signal. Furthermore, the threshold value is decreased before repeating the preceding steps of the method, if the calculated thermal load and/or calculated mechanical load of the at least one loudspeaker resulting from usage of the corrected control signal is still greater than the respective maximum load.

According to a second embodiment, the step of changing the spectrum of the control signal comprises sub-steps of allocating frequencies of the control signal to engine orders of the combustion engine, of setting amplitudes of those frequencies of the control signal to zero, the engine order of which is larger than or equal to a threshold value in order to obtain a corrected control signal, and of calculating a thermal load of the at least one loudspeaker (and especially of an oscillator coil of the at least one loudspeaker) of the anti-sound system to be expected during operation with the corrected control signal by means of a mathematical model of the at least one loudspeaker and especially oscillator coil (and especially a mathematical model of a thermal behavior of the at least one loudspeaker (and especially of the oscillator coil of the at least one loudspeaker)) and/or a mechanical load of the at least one loudspeaker (and especially of a diaphragm or spider of the at least one loudspeaker) by means of a mathematical model of the at least on loudspeaker (and especially a mathematical model of a mechanical behavior of the at least one loudspeaker (and especially of a diaphragm or spider of the at least one loudspeaker)). According to the second embodiment, the step of changing the spectrum of the control signal further comprises sub-steps of comparing the calculated thermal load and/or calculated mechanical load with a respective specified maximum load, of decreasing the threshold value and repeating the above steps, if the calculated thermal load and/or calculated mechanical load is greater than the respective maximum load, and of operating the at least one loudspeaker with the corrected control signal as soon as the calculated thermal load and/or calculated mechanical load is smaller than or equal to the respective maximum load. Thus, in this embodiment frequencies that are to be allocated to a high engine order above the threshold value are set to zero. In consequence, the spectrum of the control signal is changed to the extent that frequencies allocated to lower engine orders are retained, whereas frequencies allocated to higher engine orders are canceled.

The present invention is not limited to this, however. For reasons of the sound design, it may be useful that frequencies, which are to be allocated to lower engine orders, are set to zero and frequencies, which are to be allocated to higher engine orders, are left unchanged. In this case, the amplitudes of those frequencies of the control signal would be set to zero, the engine order of which are smaller than the threshold value, in order to obtain a corrected control signal. Furthermore, the threshold value would be increased before repeating the preceding steps of the method, if the calculated thermal load and/or calculated mechanical load of the at least one loudspeaker resulting from usage of the corrected control signal would still be greater than the respective maximum load.

In this context, the term "engine order" is defined as follows: Combustion engines are non-linear, oscillating systems. These systems have a spectrum, which apart from a fundamental frequency also has multiples of the fundamental frequency. Integer multiples are designated as harmonics. During a variable fundamental frequency, the frequencies of the multiples of the fundamental frequency vary both between each other as well as in constant ratio to the fundamental frequency. They are then designated as orders, wherein the ordinal number indicates the factor to the fundamental frequency. The second engine order, for example, is that frequency curve which corresponds to double the engine speed. Because of the step-up or step-down ratios, non-integer and in particular half-step orders are feasible in real engine systems.

According to an alternative definition that is applicable to the present invention, the "engine order" is the frequency of a periodic event in Hertz multiplied by 60 and the result being divided by the rotational speed of the engine in rpm. Thus, a periodic event (and the sound generated by this event) occurring once per rotation of a crankshaft of the engine belongs to the first engine order, for example. In this way all periodic events (and sound generated by these events) occurring in a combustion engine can be allocated to a certain engine order.

According to a third embodiment, the step of changing the spectrum of the control signal comprises the sub-steps of detecting signal components which can either be only poorly perceived or not perceived at all by the human ear, by means of a psychoacoustical model of the human ear, of setting amplitudes of those signal components of the control signal to zero the perceptibility of which by the human ear is smaller than or equal to a threshold value, in order to obtain a corrected control signal, of calculating a thermal load of the at least one loudspeaker (and especially of an oscillator coil of the at least one loudspeaker) of the anti-sound system to be expected during operation with the corrected control signal by means of a mathematical model of the at least one loudspeaker and especially oscillator coil (and especially a mathematical model of a thermal behavior of the at least one loudspeaker (and especially of the oscillator coil of the at least one loudspeaker)) and/or a mechanical load of the at least one loudspeaker (and especially of a diaphragm or spider of the at least one loudspeaker) of the anti-sound system to be expected during the operation with the corrected control signal of the anti-sound system by means of a mathematical model of the at least one loudspeaker (and especially a mathematical model of a mechanical behavior of the at least one loudspeaker (and especially of a diaphragm or spider of the at least one loudspeaker)), and of comparing the calculated thermal load and/or the calculated mechanical load with a respective specified maximum load. According to the third embodiment, the step of changing the spectrum of the control signal further comprises the sub-steps of increasing the threshold value and repeating the above steps, if the calculated thermal load and/or calculated mechanical load is larger than the respective maximum load, and of operating the at least one loudspeaker with the corrected control signal, as soon as the calculated thermal load and/or calculated mechanical load is smaller than or equal to the respective maximum load. In this manner, it is possible to specifically dispense with those signal components that would not be perceived anyway by the human ear with standard hearing capacity. Embodiments can particularly take into account the human tone audiogram for normal hearing and/or marker effects, which particularly occur with weak frequency components in the proximity of strong overtones. In this context, one can refer to the technologies described in the standard ISO/IEC 11172-3 and ISO/IEC 13818-3 (MPEG-1 Audio Layer III and MPEG-2 Audio Layer III).

According to a fourth embodiment, the step of changing the spectrum of the control signal includes the sub-steps of detecting signal components of the control signal, which are in a resonance range of the at least one loudspeaker by using a mathematical model of the a least one loudspeaker (and especially a mathematical model of a vibration behavior of the at least one loudspeaker) (the loudspeaker especially including the oscillator coil), of increasing the amplitudes of those signal components of the control signal, which are in the resonance range of the at least one loudspeaker, in order to obtain a corrected control signal, and of calculating the expected thermal load of the at least one loudspeaker (and especially of an oscillator coil of the at least one loudspeaker) of the anti-sound system to be expected during operation with the corrected control signal by means of a mathematical model of the at least one loudspeaker and especially oscillator coil (and especially a mathematical model of a thermal behavior of the at least one loudspeaker (and especially of the oscillator coil of the at least one loudspeaker)) and/or a mechanical load of the at least one loudspeaker (and especially of a diaphragm or spider of the at least one loudspeaker) of the anti-sound system during the operation with the corrected control signal by means of a mathematical model of the at least one loudspeaker (and especially a mathematical model of a mechanical behavior of the at least one loudspeaker (and especially of a diaphragm or spider of the at least one loudspeaker)). According to the fourth embodiment, the step of changing the spectrum of the control signal further includes the sub-steps of comparing the calculated thermal load and/or the calculated mechanical load with a respective specified maximum load, of reducing the amplitudes of those signal components of the control signal which are in the resonance range of the at least one loudspeaker and of repeating both of the last steps above, if the calculated mechanical load is greater than the maximum load. In this context, the extent of reducing the amplitude is not equal to the preceding raise of amplitude, i.e. larger or smaller. According to the fourth embodiment, the step of changing the spectrum of the control signal further includes the sub-steps of increasing the amplitudes of those signal components of the control signal, which are in the resonance range of the at least one loudspeaker once again and of repeating the two last steps above, if the calculated mechanical load is smaller than or equal to the maximum load and at the same time the calculated thermal load is greater than the maximum load. As soon as the calculated thermal load and/or calculated mechanical load are smaller than or equal to the respective maximum load, a step follows of operating the at least one loudspeaker with the corrected control signal.

By increasing the amplitudes of those signal components of the control signal which are in the resonance range of the at least one loudspeaker, a slight increase of the amplitudes of individual signal components produces a superproportional deflection of the respective loudspeaker diaphragm. As a result, the airflow conducted past the oscillator coil of the loudspeaker increases, and the self-cooling of the oscillator coil therefore increases to an extent which overcompensates the additional temperature increase of the oscillator coil due to the increase in amplitude. Accordingly, a slight reduction of those signal components of the control signal, which are in the resonance range of the at least one loudspeaker, results in a superproportional decrease of the deflection of the respective loudspeaker diaphragm.

In embodiments, the specified maximum load is a temperature value and/or a maximum deflection of the diaphragm of the at least one loudspeaker and is therefore a time-independent value.

Pursuant to alternative embodiments, the specified maximum load is a function of temperature and duration and/or a function of a maximum deflection of a diaphragm of the at least one loudspeaker and a frequency of occurrence. The maximum load is therefore exceeded only then, when a temperature value is exceeded for a certain minimum period, and/or a maximum deflection occurs too frequently within a time interval. For this purpose, the collective of temperature and/or deflection can be evaluated according to the rules of the linear accumulation of damage. In this manner, transient loads, which do not yet impair the service life of the respective loudspeaker, can be tolerated.

According to embodiments, the mathematical model of the at least one loudspeaker and especially oscillator coil (and especially the mathematical model of a thermal behavior of the at least one loudspeaker (and especially of the oscillator coil of the at least one loudspeaker)) takes into account at least one of the parameters from ambient temperature, atmospheric pressure, air humidity, signal of a rain sensor, exhaust gas temperature, engine speed, engine torque, and the airflow against the respective loudspeaker when driving. For this purpose, the air humidity can be used to adapt the heat capacity of the air surrounding the respective loudspeaker. The output signal of the rain sensor permits a confidence region for the outside temperature and air humidity. Some or all of the above values can be provided on a CAN bus of an engine control unit of a vehicle.

Embodiments of an anti-sound system for exhaust systems of a vehicle driven by a combustion engine have an anti-sound control unit, at least one loudspeaker, and an error microphone. For this purpose, the at least one loudspeaker is connected with the anti-sound control unit for the reception of control signals and adapted to produce anti-sound in a sound generator, which can be placed in a fluid connection with the exhaust system, depending on the control signals received from the anti-sound control unit. The error microphone is furthermore connected with the anti-sound control unit and is arranged in a position of the exhaust system situated in the vicinity of the fluid connection between sound generator and exhaust system, and is adapted to measure sound within the exhaust system and to provide a corresponding measuring signal to the anti-sound control unit. In this context, "in the vicinity of the fluid connection" means that the error microphone is at a distance from the fluid connection between the sound generator and the exhaust system downstream or upstream on this fluid connection along the exhaust gas flow that is not more than ten times and particularly not more than five times and more particularly not more than double of the maximum diameter of the exhaust system at this fluid connection along the exhaust gas flow. The anti-sound control unit is adapted for executing the method described above, in order to cancel signals received from the error microphone (and thus airborne sound conducted in the exhaust system) at least partially and preferably completely both in value and phase by outputting the control signal to the at least one loudspeaker. This sound cancellation should be audible and measurable at least outside of the exhaust system, but preferably also within the exhaust system.

Embodiments of a vehicle comprise a combustion engine, an exhaust system that has a fluid connection with the combustion engine, and the anti-sound system described above, wherein the sound generator is connected with the exhaust system and the error microphone is arranged in or on the exhaust system.

In this context it is pointed out that in this document, unless not specifically explicitly stated otherwise, the term "control" is used overall synonymously with the term "regulate," other than what is commonly used in the German language. This also concerns all grammatical variations of both terms. In this document, the term "control" can therefore comprise a reference to a control variable and/or its measuring value, same as the term "regulation" can also refer to a simple control chain.

Moreover, it is pointed out that the terms used in this specification and in the claims for the enumeration of features, such as "encompass," "comprise," "include," "contain" and "with," as well as their grammatical variations, are generally to be understood as a non-conclusive enumeration of features, such as method steps, equipment, areas, factors and suchlike, and by no means excludes the existence of other or additional features or groupings of other or additional features.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

Further features of the invention result from the subsequent description of embodiments in conjunction with the claims and the figures. In the figures, the same and/or similar elements are designated with the same and/or similar reference symbols. It is pointed out that the invention is not limited to the embodiments of the described examples of embodiments, but is determined by the scope of the enclosed claims. In particular, the individual features of the embodiments as taught by the invention can be realized in a different quantity and combination than in the examples cited below. In the following explanation of some embodiments of the invention, reference is also made to the enclosed Figures, of which:

DESCRIPTION OF THE PREFERRED EMBODIMENTS

Figure 1:
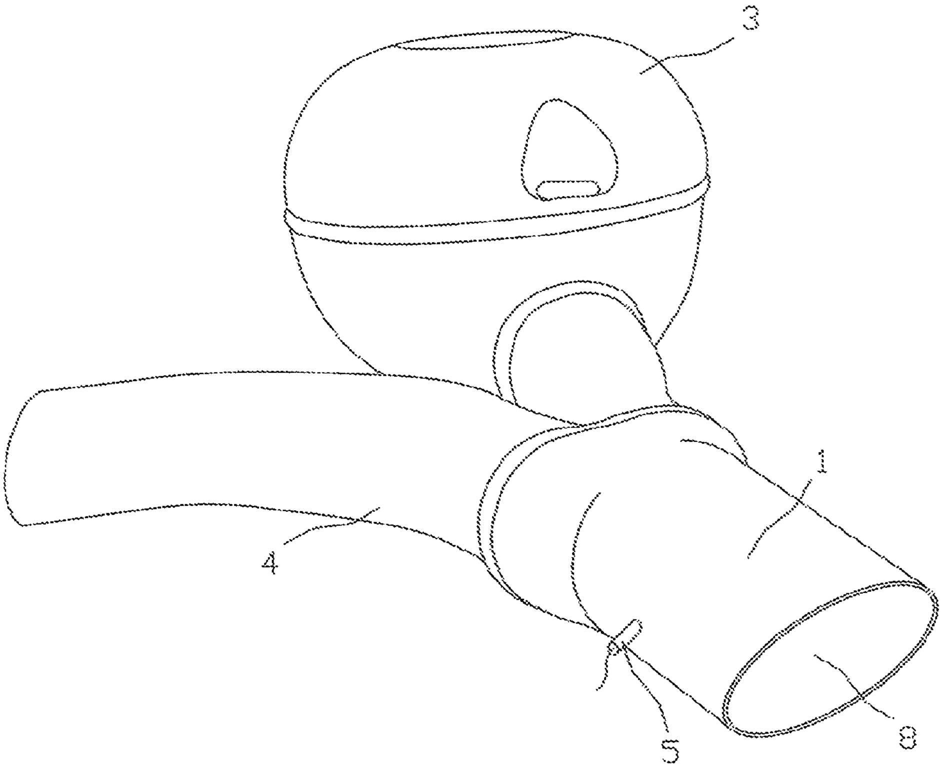
FIG. 1 is a schematic and perspective view of an anti-sound system according to an embodiment of the invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

It should be noted in this context that the terms "comprise", "include", "having" and "with", as well as grammatical modifications thereof used in this specification or in the claims, indicate the presence of technical features such as stated components, figures, integers, steps or the like, and by no means preclude the presence or addition of one or more alternative features, particularly other components, figures, integers, steps or groups thereof.

Figure 2:
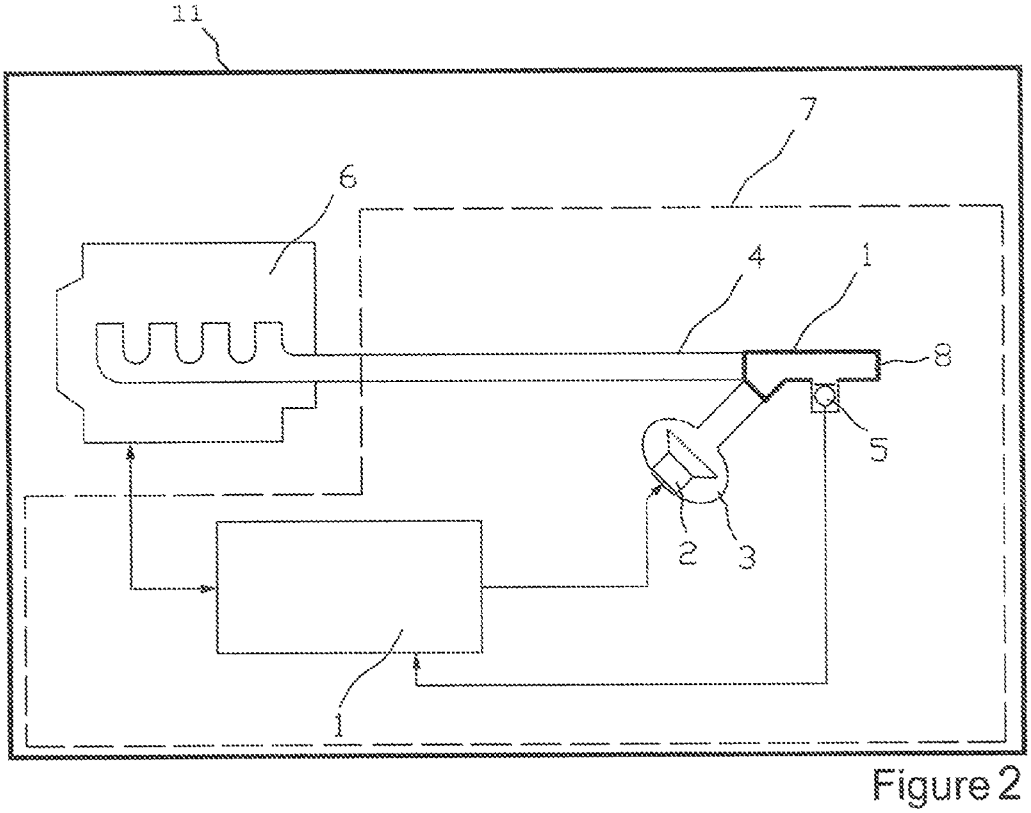
FIG. 2 is a schematic block diagram of the anti-sound system from FIG. 1 in interaction with an exhaust system of a combustion engine of a vehicle.

An anti-sound system 7 according to an embodiment of the invention is subsequently described with reference to the FIGS. 1 and 2.

The anti-sound system 7 comprises a sound generator 3 in the form of a sound-insulated housing, which contains a loudspeaker 2 and is in fluid connection with an exhaust system 4 in the vicinity of a tailpipe 1.

The tailpipe 1 has an opening 8 to discharge exhaust gas conducted in the exhaust system 4 to the outside.

An error microphone 5 in the form of a pressure sensor is provided on the tailpipe 1. The error microphone 5 measures pressure fluctuations and therefore sound inside of the tailpipe 1 in a section downstream of an area, in which the fluid connection between the exhaust system 4 and the sound generator 3 is provided. It is emphasized, however, that the present invention is not limited to such type of arrangement of the error microphone. Generally it is sufficient, if the error microphone is at a distance downstream or upstream with reference to the exhaust gas flow from the fluid connection between the sound generator and the exhaust system that is not more than ten times and particularly not more than five times and more particularly not more than double of the maximum diameter of the exhaust system at this fluid connection.

The loudspeaker 2 and the error microphone 5 are electrically connected with an anti-sound control unit 10.

The exhaust system 4 can furthermore comprise a catalytic converter (not shown) positioned between a combustion engine 6 and the tailpipe 1 for purifying the exhaust gas emitted from the combustion engine 6 and conducted in the exhaust system 4.

The combustion engine 6 and the anti-sound system 7 are integrated into a vehicle 11. Components of the vehicle 11 that are of no significance with respect to the present invention such as a carriage including wheels, user interfaces such as a steering wheel etc. are not shown in the Figures.

The functionality of the above anti-sound system 7 will subsequently be explained in greater detail by means of the flow diagrams from FIGS. 3, 4A, 4B, 4C and 4D.

Figure 3:
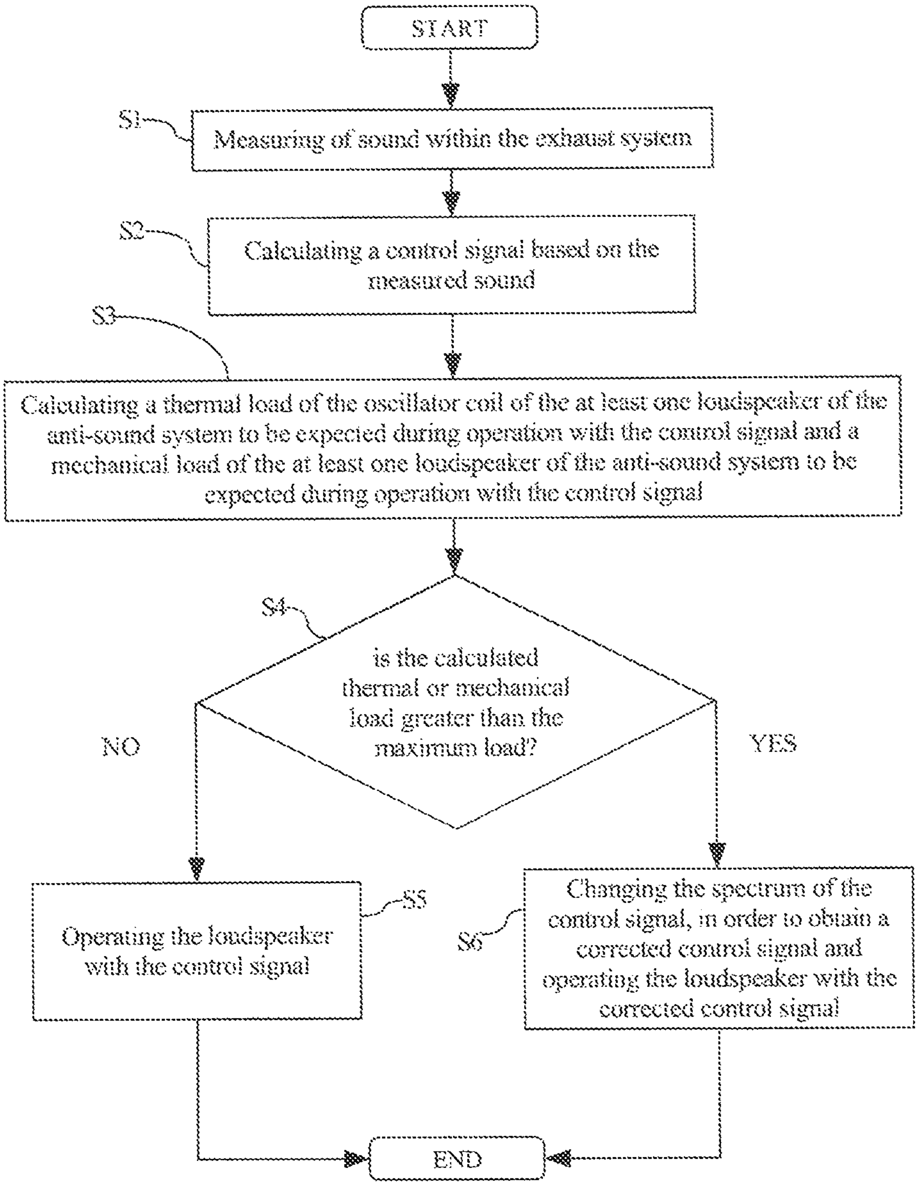
FIG. 3 is a flow diagram of a method for controlling the anti-sound system for exhaust systems from FIGS. 1 and 2 according to a general embodiment.

The general principle of operation of the anti-sound control unit 10 is shown in FIG. 3.

Initially, in step S1, the sound that is conducted inside of the exhaust system is measured by means of the error microphone 5 in the vicinity of the tailpipe 1.

In the following step S2, the anti-sound control unit 10 calculates a control signal by means of the measured sound, using a Filtered-x Least Mean Squares (FxLMS) algorithm, where said control signal permits extensive cancellation of the sound carried inside of the exhaust system, by application with anti-sound.

Thereafter (S3), the anti-sound control unit 10 calculates the thermal load of an oscillator coil of the loudspeaker 2 which is to be expected during operation with the control signal, using a mathematical model of the oscillator coil (and especially of the thermal behavior of the oscillator coil) which is stored in the anti-sound control unit. In this context, the model of the loudspeaker 2 described in WO 02/21879 is used, wherein the ambient temperature of a vehicle which holds the anti-sound system 7, the ambient temperature of the loudspeaker 2, the current atmospheric pressure, the current air humidity, the exhaust gas temperature, the engine speed, the engine torque, as well as the airflow against the loudspeaker that is to be expected from driving because of the vehicle geometry and vehicle speed are additionally taken into account in the model. In this context, for the confidence region of air humidity and ambient temperature, the output signal of a rain sensor of the vehicle is also used. The mathematical model can also be available in the form of a characteristic line or table, for example, instead of in the form of a formula. The anti-sound control unit 10 determines the air humidity and the exhaust gas temperature by means of suitable sensors (not shown), and the engine speed, the engine torque, the output signal of the rain sensor as well as the vehicle speed are provided to the anti-sound control unit 10 by an engine control unit of the engine 6 via a CAN bus.

By taking into account the parameters provided by the engine control unit via the CAN bus, it is possible to anticipate the future temperature development of the oscillator coil that is to be expected. If the engine speed increases drastically, for example, it can be expected that the exhaust gas temperature will increase with little delay, or if the vehicle speed decreases drastically, it can be expected that the cooling of the loudspeaker by the ambient air will be reduced. This makes it possible to operate the oscillator coil by taking into account future thermal loads as a preventative measure, since future temperature increases of the oscillator coil due to external parameters such as increased exhaust gas temperature or reduced cooling, can be predicted. Consequently, by using the above parameters, the mathematical model of the oscillator coil can dynamically take into account the operational state of the vehicle and the engine.

At the same time, the anti-sound control unit 10 in step S3 calculates the mechanical load of a membrane and spider of the loudspeaker 2 to be expected during operation with the control signal, using a mathematical model of the loudspeaker (and especially a mathematical model of the mechanical behavior of the loudspeaker) which is stored in the anti-sound control unit.

In step S4, the calculated thermal load of the oscillator coil and the calculated mechanical load of the loudspeaker are compared with a respective specified maximum load. For this purpose, separate maximum loads are specified for the thermal load and the mechanical load, respectively.

In the embodiment shown, this thermal maximum load is specified not as a simple temperature value, but as a function of temperature and duration. The anti-sound control unit 10 therefore takes into account the history of the load of the oscillator coil, so that it is permissible if the temperature of the oscillator coil is briefly exceeded, as long as the expected overall service life of the loudspeaker 2 is not affected as a result.

Also the mechanical maximum load is not simply a maximum deflection of the diaphragm and spider of the loudspeaker, but rather a function of deflection and frequency of occurrence.

If the calculated thermal load and calculated mechanical loads are smaller or equal to the respective maximum load, the loudspeaker is operated (S5) with the control signal calculated by the anti-sound control unit in step S2.

Otherwise, if the calculated thermal or mechanical load is greater than the maximum load, the spectrum of the control signal is changed in step S6, in order to obtain a corrected control signal, and the loudspeaker 2 will be operated with the corrected control signal.

Even if FIG. 3 only shows one pass through the control loop of the anti-sound control unit 10, it is obvious for one skilled in the art, that this control loop will subsequently be immediately repeated in practical applications due to a changed spectrum of the sound conducted in the exhaust system 5, as a result of changed engine speed, for example.

Four alternative embodiments of step S6 are shown in FIGS. 4A, 4B, 4C and 4D.

Figure 4A:
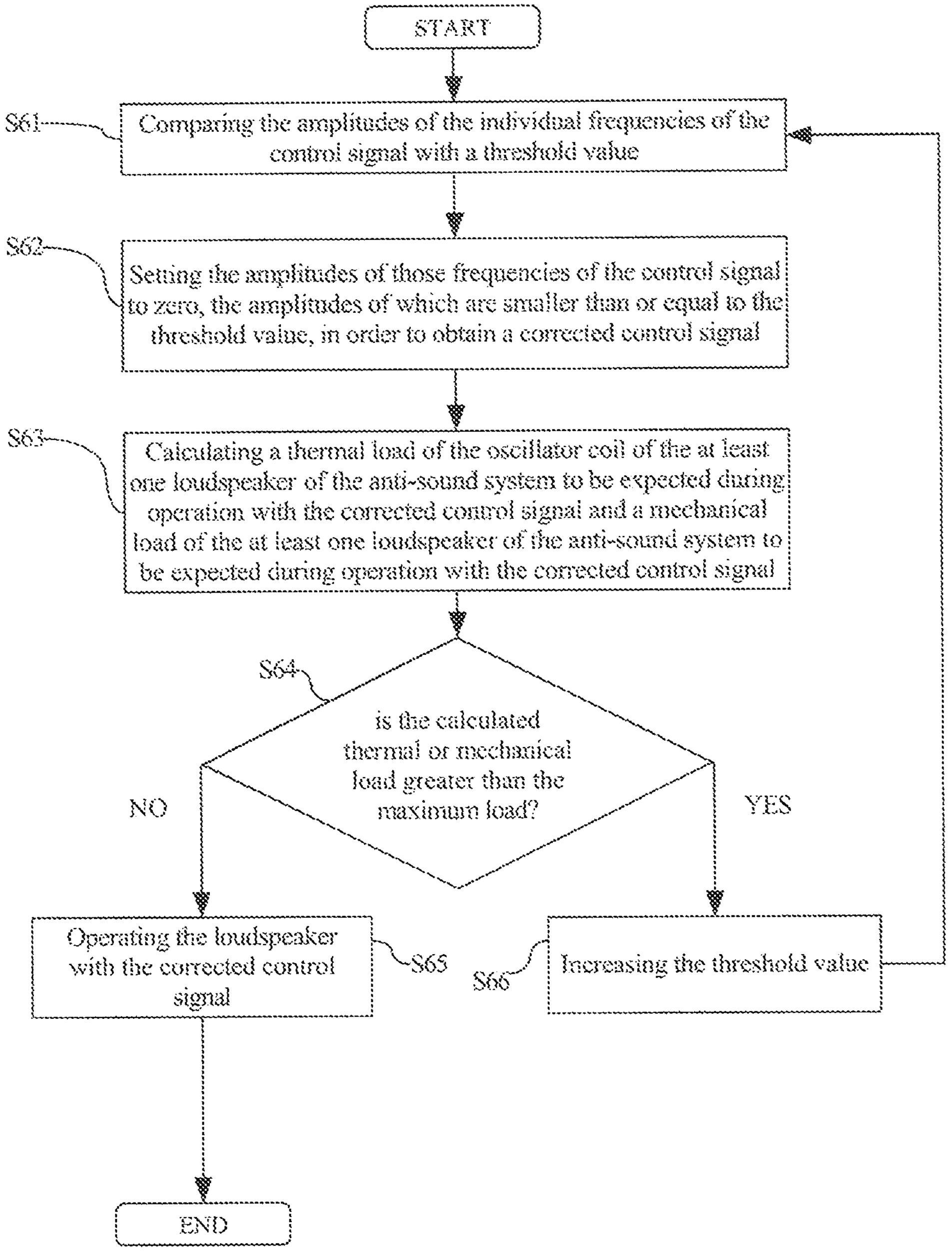
FIG. 4A is a flow diagram of a method for controlling the anti-sound system for exhaust systems from FIGS. 1 and 2 according to a first embodiment.

According to a first embodiment shown in FIG. 4A, in a first step S61, initially amplitudes of individual frequencies of the control signal are compared with an initial threshold value stored in the anti-sound control unit 10.

Subsequently the amplitudes of those frequencies of the control signal are set to zero, of which the amplitudes are smaller or equal to the threshold value, in order to obtain a corrected control signal (S62).

In the following step S63, the anti-sound control unit 10 calculates a thermal load of the oscillator coil of the loudspeaker 2 of the anti-sound system 7 to be expected during operation with the corrected control signal by using the mathematical model of the oscillator coil (and especially the mathematical model of the thermal behavior of the oscillator coil), as well as a mechanical load of a diaphragm and spider of the loudspeaker 2 of the anti-sound system 7 to be expected during operation with the corrected control signal by using the mathematical model of the loudspeaker (and especially the mathematical model of the mechanical behavior of the loudspeaker) stored in the anti-sound control unit 10. This calculation is performed analogously to the calculation in step S3 from FIG. 3.

Thereafter, the calculated thermal load and the calculated mechanical load are compared in step S64 with a respective specified maximum load set in the anti-sound control unit 10, depending on a loudspeaker 2 used in each case. This comparison is performed analogously to the comparison in step S4 from FIG. 3.

If the calculated thermal load or calculated mechanical load is greater than the respective maximum load, the threshold value in step S66 is increased, and the method returns to step S61.

On the other hand, if the calculated thermal load and the calculated mechanical load both are smaller than or equal to the maximum load, the loudspeaker 2 is operated with the corrected control signal in step S65.

Figure 4B:
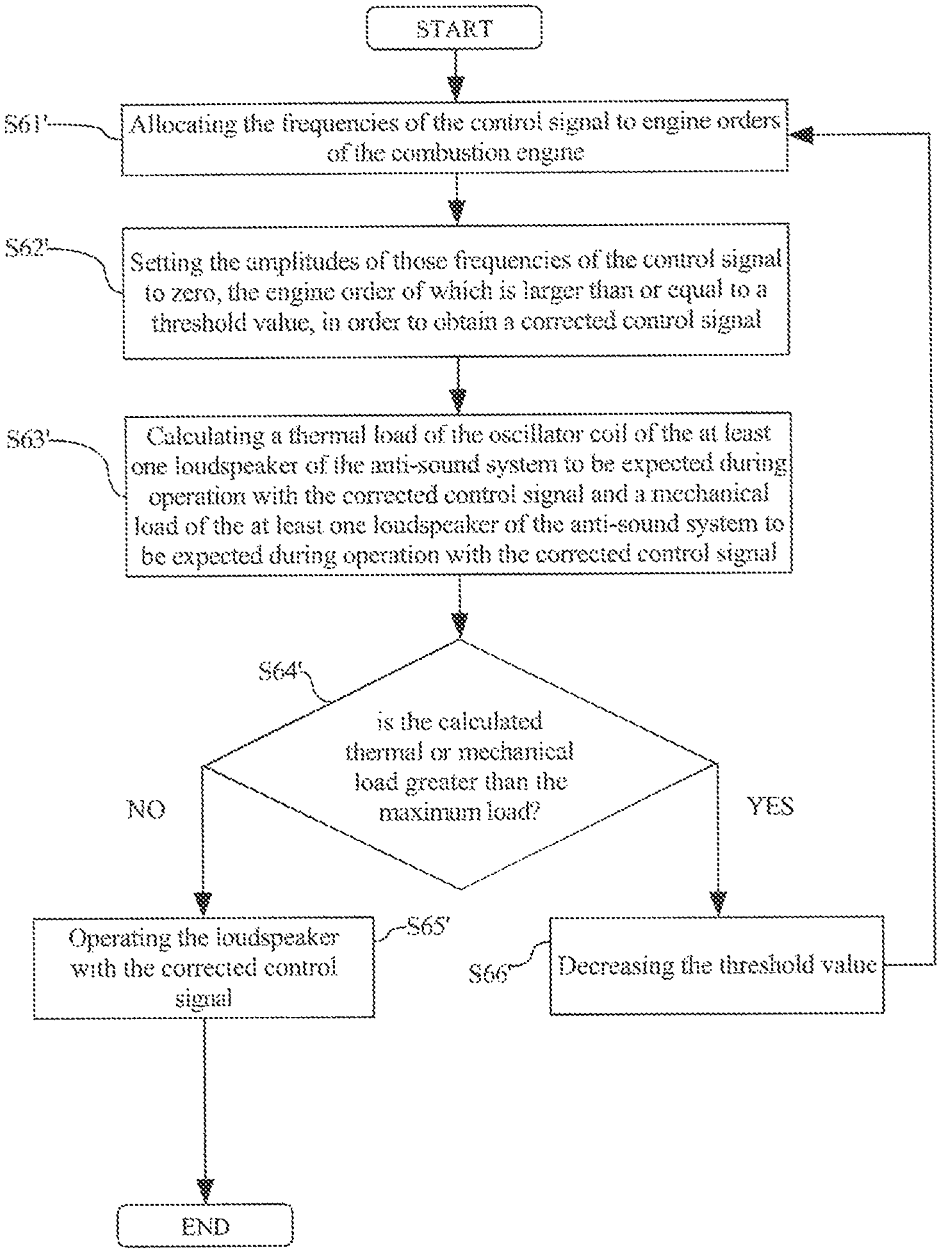
FIG. 4B is a flow diagram of a method for controlling the anti-sound system for exhaust systems from FIGS. 1 and 2 according to a second embodiment.

According to a second embodiment shown in FIG. 4B, initially frequencies of the control signal are allocated to engine orders of the combustion engine 6 in a first step S61'. In the illustrated embodiment, this allocation is performed using multiples of the engine speed.

In the following step S62', amplitudes of those frequencies of the control signal are set to zero, the engine order of which is larger than or equal to an initial threshold value that is stored in the anti-sound control unit 10, in order to obtain a corrected control signal.

Subsequently, a thermal load of the oscillator coil of the loudspeaker 2 of the anti-sound system 7 to be expected during operation with the corrected control signal is calculated by using the mathematical model of the oscillator coil (and especially the mathematical model of the thermal behavior of the oscillator coil) as well as a mechanical load of a diaphragm and spider of the loudspeaker 2 of the anti-sound system 7 to be expected during operation with the corrected control signal is calculated by using the mathematical model of the loudspeaker 2 (and especially the mathematical model of the mechanical behavior of the loudspeaker) stored in the anti-sound control unit 10 (S63'). This calculation is performed analogously to the calculation in step S3 from FIG. 3.

In the following step S64', the calculated thermal load and the calculated mechanical load are compared with a respective specified maximum load specified in the anti-sound control unit 10, depending on a loudspeaker 2 used in each case. This comparison is performed analogously to the comparison in step S4 from FIG. 3.

If the calculated thermal load or the calculated mechanical load is greater than the maximum load, the threshold value is reduced in step S66', before the method returns to step S61'.

Otherwise, as soon as both the calculated thermal load and the calculated mechanical load are smaller than or equal to the respective maximum load, the loudspeaker 2 is operated with the corrected control signal in step S65'.

Figure 4C:
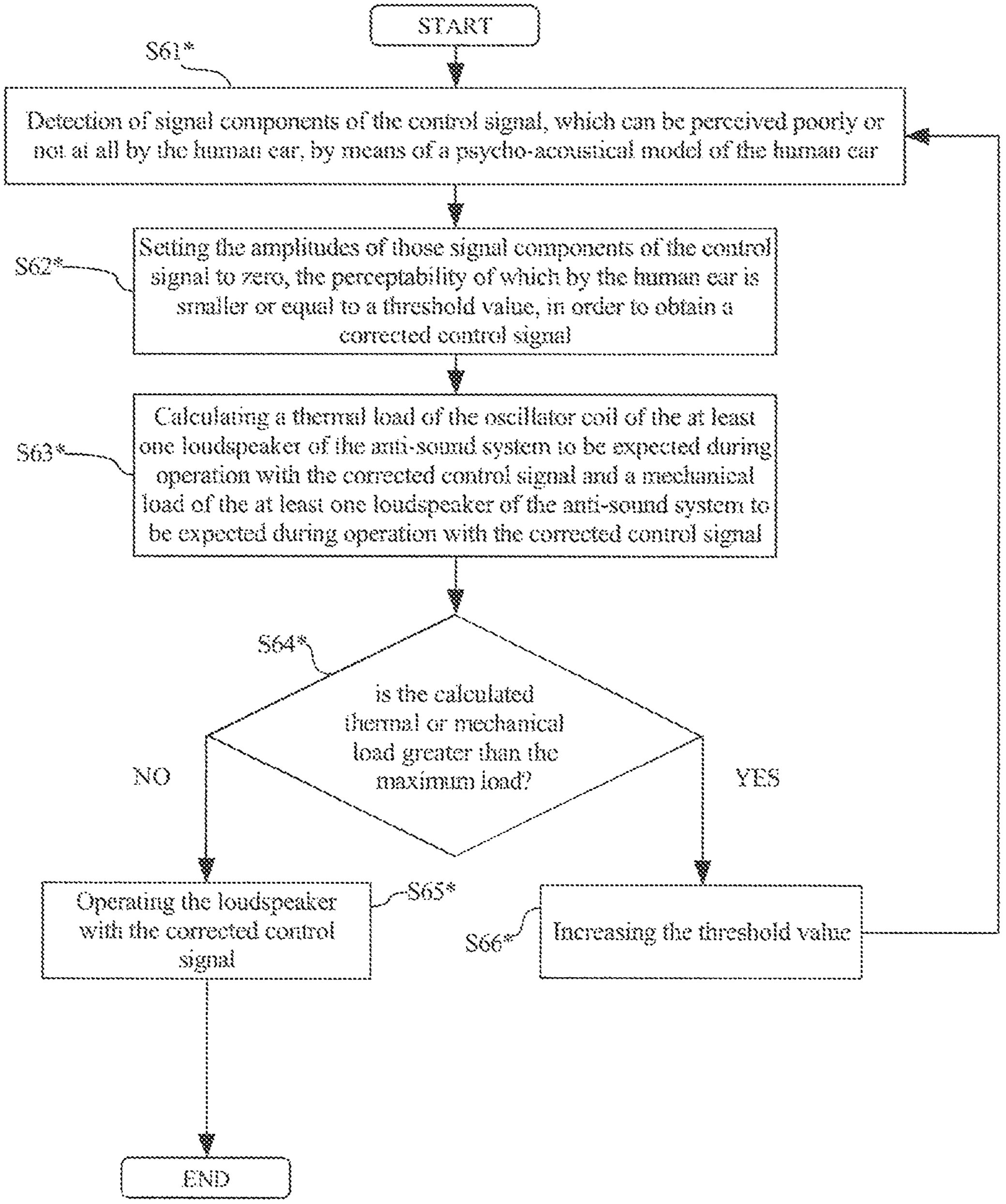
FIG. 4C is a flow diagram of a method for controlling the anti-sound system for exhaust systems from FIGS. 1 and 2 according to a third embodiment.

According to a third embodiment shown in FIG. 4C, initially in a first step S61*, using a psychoacoustical model of the human ear, signal components of the control signal are detected, which can be perceived either poorly or not at all by the human ear. In the present embodiment this detection is done analogously to the ISO/IEC 11172-3 and ISO/IEC 13818-3 standard.

In the following step S62*, amplitudes of those frequencies of the control signal are set to zero, the perceptibility of which by the human ear is smaller than or equal to a threshold value, in order to obtain a corrected control signal.

Subsequently, a thermal load of the oscillator coil of the loudspeaker 2 of the anti-sound system 7 to be expected during operation with the corrected control signal is calculated by using the mathematical model of the oscillator coil (and especially the mathematical model of the thermal behavior of the oscillator coil) as well as a mechanical load of a diaphragm and spider of the loudspeaker 2 of the anti-sound system 7 to be expected during operation with the corrected control signal is calculated by using the mathematical model of the loudspeaker 2 (and especially the mathematical model of the mechanical behavior of the loudspeaker) stored in the anti-sound control unit 10 (S63*). This calculation is performed analogously to the calculation in step S3 from FIG. 3.

In the following step S64*, the calculated thermal load and the calculated mechanical load are both compared with a respective maximum load specified in the anti-sound control unit 10, depending on a loudspeaker 2 used in each case. This comparison is performed analogously to the comparison in step S4 from FIG. 3.

If the calculated thermal load or the calculated mechanical load is greater than the maximum load, the threshold value is increased in step S66*, before the method returns to step S61*.

Otherwise, as soon as both the calculated thermal load and the calculated mechanical load are smaller than or equal to the maximum load, the loudspeaker 2 in step S65* is operated with the corrected control signal.

Figure 4D:
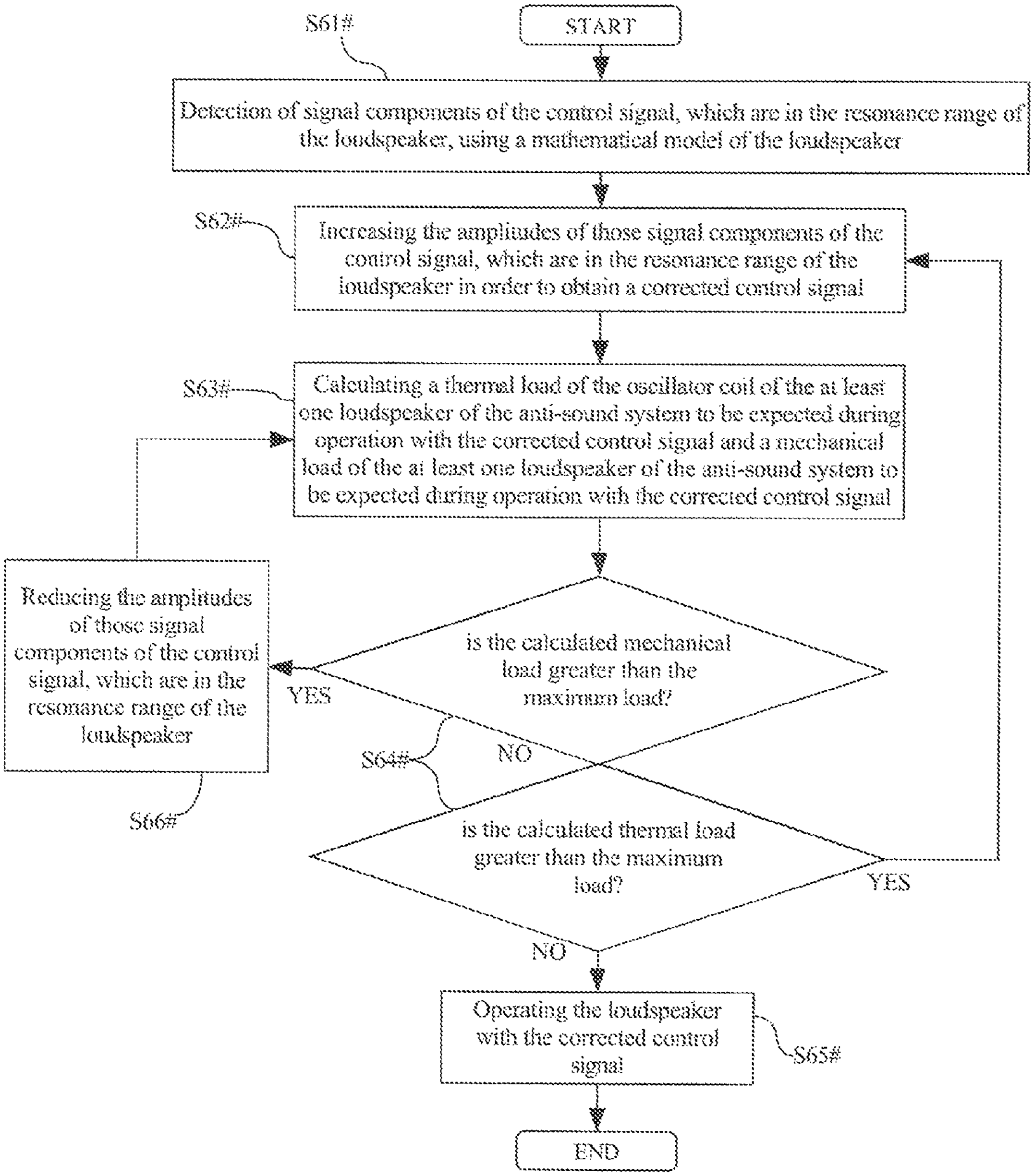
FIG. 4D is a flow diagram of a method for controlling the anti-sound system for exhaust systems from FIGS. 1 and 2 according to a fourth embodiment.

According to a fourth embodiment shown in FIG. 4D, in a first step S61#, using a mathematical model of the loudspeaker comprising the oscillator coil and especially a mathematical model of the vibration behavior of the loudspeaker, signal components of the control signal are detected which are in resonance range of the loudspeaker.

Subsequently, in step S62#, amplitudes of those signal components of the control signal which are in the resonance range of the loudspeaker are raised and increased, in order to obtain a corrected control signal. In the present embodiment this raise occurs by a specified absolute value. Alternatively, this raise can also occur by a specified relative value the amount of which relative value depends on the absolute value of the respective amplitude.

In the following step S63#, the respective expected thermal load of the oscillator coil of the loudspeaker of the anti-sound system when operated with the corrected control signal is calculated by using the mathematical model of the oscillator coil (and especially the mathematical model of the thermal behavior of the oscillator coil) and an expected mechanical load of the loudspeaker of the anti-sound system when operated with the corrected control signal is calculated by using a mathematical model of the loudspeaker (and especially the mathematical model of the mechanical behavior of the loudspeaker).

Then, a comparison (S64#) of both the calculated thermal load and the calculated mechanical load with a specified maximum load follows.

If the calculated mechanical load is greater than the maximum load, the amplitudes of those signal components of the control signal which are in the resonance range of the loudspeaker are decreased again and therefore lowered in the following step S66#, before steps S63# to S64# are repeated again. In the embodiment shown, this decrease occurs by a specified absolute value which corresponds to half of the absolute value used for the preceding increase in step S62#. Alternatively, this decrease can for example also occur by a specified relative value depending on the value that was used for the value in step S62# for the preceding raise. What is crucial is that the decrease is not the same as the preceding increase, and vice versa.

If the calculated mechanical load is smaller than or equal to the maximum load, but the calculated thermal load is still greater than the maximum load, however, steps S62# to S64# are repeated.

As soon as both the calculated thermal load and the calculated mechanical load are smaller than or equal to the maximum load, the loudspeaker is operated with the corrected control signal (S65#).

Even if in the above embodiments described with reference to FIGS. 4A, 4B, 4C and 4D both the thermal load of the oscillator coil as well as the mechanical load of the loudspeaker were considered, as a deviation thereof also only one of the thermal load of the oscillator coil and of the mechanical load of the loudspeaker can be considered, and the other load can be disregarded in each case.

For the sake of clear representation, only those elements, components and functions are represented in the Figures that are required to understand the present invention.

Embodiments of the invention are however not limited to the illustrated elements, components and functions, but they contain additional elements, components and functions, to the extent that they are necessary for their use or their scope of functionality.

Even if the invention was described above using a maximum of two control signals, the present invention is not limited thereto. The invention can rather be broadened to any number of control signals.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A method for controlling an anti-sound system for an exhaust system of a vehicle operated by a combustion engine, for generating an anti-airborne sound in the exhaust system based on measured sound, in order to cancel airborne sound generated by the combustion engine and conducted in the exhaust system in the vicinity of the position in the exhaust system at which the sound is measured at least partially and preferably completely in amount and phase, the method comprising the steps of:

measuring sound inside the exhaust system;

calculating a control signal based on the measured sound;

calculating at least one of an expected thermal load of the least one loudspeaker of the anti-sound system during the operation with the control signal based on a mathematical model of a thermal behavior of the loudspeaker and an expected mechanical load of the at least one loudspeaker of the anti-sound system during the operation with the control signal based on a mathematical model of a mechanical behavior the loudspeaker;

comparing the calculated expected thermal load or the calculated expected mechanical load with a specified maximum load;

operating the loudspeaker with the control signal, if the calculated expected thermal load or the calculated expected mechanical load is smaller than or equal to the maximum load; and changing a spectrum of the control signal to obtain a corrected control signal if the calculated thermal load or the calculated mechanical load is greater than the maximum load, and operating the loudspeaker with the corrected control signal.

2. The method according to claim 1, wherein the step of changing the spectrum of the control signal comprises the following sub-steps:

comparing amplitudes of individual frequencies of the control signal with a threshold value;

setting amplitudes of individual frequencies of the control signal, which amplitudes of individual frequencies are smaller than or equal to the threshold value, to zero in to obtain the corrected control signal;

calculating at least one of an expected thermal load of the at least one loudspeaker of the anti-sound system during the operation with the corrected control signal based on a mathematical model of a thermal behavior of the loudspeaker and an expected mechanical load of the at least one loudspeaker of the anti-sound system, based on a mathematical model of a mechanical behavior the loudspeaker;

comparing the calculated expected thermal load or the calculated expected mechanical load with the specified maximum load;

increasing the threshold value and repeating the sub-steps of comparing amplitudes, setting amplitudes, calculating at least one of an expected thermal load and expected mechanical load, and comparing the calculated expected thermal load or the calculated expected mechanical load if the calculated expected thermal load or the calculated expected mechanical load is greater than the maximum load; and operating the loudspeaker with the corrected control signal, upon the calculated expected thermal load or the calculated expected mechanical load being smaller than or equal to the maximum load.

3. The method according to claim 1, wherein the step of changing the spectrum of the control signal comprises the following sub-steps:

allocating frequencies of the control signal to engine orders of the combustion engine;

setting amplitudes of those frequencies of the control signal, the allocated engine order of which are greater than or equal to a threshold value, to zero in order to obtain a corrected control signal;

calculating at least one of an expected thermal load of the at least one loudspeaker of the anti-sound system during operation with the corrected control signal based on a mathematical model of a thermal behavior of the loudspeaker and an expected mechanical load of the at least one loudspeaker of the anti-sound system during operation with the corrected control signal based on a mathematical model of a mechanical behavior the loudspeaker;

comparing the calculated expected thermal load or the calculated mechanical expected load with the specified maximum load;

decreasing the threshold value and repeating the sub-steps of allocating frequencies, setting amplitudes, calculating at least one of an expected thermal load and expected mechanical load, and comparing the calculated expected thermal load or the calculated mechanical expected load, if the calculated thermal load or the calculated mechanical load is greater than the maximum load; and operating the loudspeaker with the corrected control signal upon the calculated expected thermal load or the calculated expected mechanical load being smaller than or equal to the maximum load.

4. The method according to claim 1, wherein the step of changing the spectrum of the control signal comprises the following sub-steps:

detecting signal components of the control signal that are perceived poorly or not at all by the human ear, using a psychoacoustical model of the human ear;

setting amplitudes of the detected signal components of the control signal, the perceptibility of which by the human ear is smaller than or equal to a threshold value, to zero in order to obtain a corrected control signal;

calculating at least one of an expected thermal load of the at least one loudspeaker of the anti-sound system during operation with the corrected control signal based on a mathematical model of a thermal behavior of the loudspeaker or an expected mechanical load of the at least one loudspeaker of the anti-sound system during operation with the corrected control signal, based on a mathematical model of a mechanical behavior the loudspeaker;

comparing the calculated thermal load or calculated mechanical load with the specified maximum load;

increasing the threshold value and repeating the sub-steps of detecting signal components, setting of amplitudes, calculating at least one of an expected thermal load or an expected mechanical load and comparing the calculated thermal load or calculated mechanical load, if the calculated thermal load or the calculated mechanical load is greater than the maximum load; and operating the loudspeaker with the corrected control signal, upon the calculated thermal load or the calculated mechanical load being smaller than or equal to the maximum load.

5. The method according to claim 1, wherein the step of changing the spectrum of the control signal comprises the following sub-steps:

detecting signal components of the control signal which are in a resonance range of the loudspeaker, using a mathematical model of a vibration behavior of the loudspeaker;

increasing the amplitudes of those signal components of the control signal, which are in the resonance range of the loudspeaker, to obtain a corrected control signal;

calculating at least one of an expected thermal load of the at least one loudspeaker of the anti-sound system during operation with the corrected control signal based on a mathematical model of a thermal behavior of the loudspeaker and an expected mechanical load of the at least one loudspeaker of the anti-sound system during operation with the corrected control signal, based on a mathematical model of a mechanical behavior the loudspeaker;

comparing the calculated thermal load or the calculated mechanical load with the specified maximum load;

reducing amplitudes of signal components of the control signal, which are in the resonance range of the loudspeaker and repeating the sub-steps calculating at least one of an expected thermal load or an expected mechanical load, and comparing the calculated thermal load or the calculated mechanical load, if the calculated expected mechanical load is larger than the maximum load, and repeating the steps of increasing the amplitudes, calculating at least one of an expected thermal load or an expected mechanical load, and comparing the calculated thermal load or the calculated mechanical load, if the calculated expected thermal load is greater than the maximum load; and operating the loudspeaker with the corrected control signal, as soon as the calculated thermal load or the calculated mechanical load is smaller than or equal to the maximum load.

6. The method according to claim 1, wherein the specified maximum load is at least one of a temperature value and a maximum deflection of a diaphragm of the loudspeaker.

7. The method according to claim 1, wherein the specified maximum load is at least one of:
a function of temperature and duration; and
a function of a maximum deflection of a diaphragm of the loudspeaker and a frequency of occurrence.

8. The method according to claim 1, wherein the mathematical model of the thermal behavior of the loudspeaker takes into account at least one of the following parameters:
ambient temperature;
atmospheric pressure;
air humidity;
signal of a rain sensor;
exhaust gas temperature;
engine speed;
engine torque; and
air flow against the loudspeaker from driving.

9. The method according to claim 2, wherein the specified maximum load is at least one of a temperature value and a maximum deflection of a diaphragm of the loudspeaker.

10. The method according to claim 2, wherein the specified maximum load is at least one of:
a function of temperature and duration; and
a function of a maximum deflection of a diaphragm of the loudspeaker and a frequency of occurrence.

11. The method according to claim 2, wherein the mathematical model of the thermal behavior of the loudspeaker takes into account at least one of the following parameters:
ambient temperature;
atmospheric pressure;
air humidity;
signal of a rain sensor;
exhaust gas temperature;
engine speed;
engine torque; and
air flow against the loudspeaker from driving.

12. The method according to claim 3, wherein the specified maximum load is at least one of a temperature value and a maximum deflection of a diaphragm of the loudspeaker.

13. The method according to claim 3, wherein the specified maximum load is at least one of:
a function of temperature and duration; and
a function of a maximum deflection of a diaphragm of the loudspeaker and a frequency of occurrence.

14. The method according to claim 3, wherein the mathematical model of the thermal behavior of the loudspeaker takes into account at least one of the following parameters:
ambient temperature;
atmospheric pressure;
air humidity;
signal of a rain sensor;
exhaust gas temperature;
engine speed;
engine torque; and
air flow against the loudspeaker from driving.

15. The method according to claim 4, wherein the specified maximum load is at least one of a temperature value and a maximum deflection of a diaphragm of the loudspeaker.

16. The method according to claim 4, wherein the specified maximum load is at least one of:
a function of temperature and duration; and
a function of a maximum deflection of a diaphragm of the loudspeaker and a frequency of occurrence.

17. The method according to claim 4, wherein the mathematical model of the thermal behavior of the loudspeaker takes into account at least one of the following parameters:
ambient temperature;
atmospheric pressure;
air humidity;
signal of a rain sensor;
exhaust gas temperature;
engine speed;
engine torque; and
air flow against the loudspeaker from driving.

18. The method according to claim 5, wherein the specified maximum load is at least one of a temperature value and a maximum deflection of a diaphragm of the loudspeaker.

19. The method according to claim 5, wherein the specified maximum load is at least one of:
a function of temperature and duration; and
a function of a maximum deflection of a diaphragm of the loudspeaker and a frequency of occurrence.

20. The method according to claim 5, wherein the mathematical model of the thermal behavior of the loudspeaker takes into account at least one of the following parameters:
ambient temperature;
atmospheric pressure;
air humidity;
signal of a rain sensor;
exhaust gas temperature;
engine speed;
engine torque; and
air flow against the loudspeaker from driving.

21. An anti-sound system for an exhaust system of a vehicle operated by a combustion engine, the anti-sound system comprising:
an anti-sound control unit;
a loudspeaker operatively connected to the anti-sound control unit for the reception of control signals, wherein the loudspeaker is adapted for generating an anti-sound in a sound generator which can be placed in a fluid connection with the exhaust system, wherein the generation of anti-sound by the loudspeaker is dependant upon a control signal received by the loudspeaker from the anti-sound control unit; and
an error microphone operatively connected with the anti-sound control unit and arranged in a position of the exhaust system with reference to exhaust gas flow situated in the vicinity of the fluid connection between the sound generator and the exhaust system, wherein the error microphone is adapted to measure sound within the exhaust system, and to provide a corresponding output measuring signal to the anti-sound control unit;
wherein the anti-sound control unit is adapted to execute the steps of:
measuring sound inside the exhaust system;
calculating a control signal based on the measured sound;
calculating at least one of an expected thermal load of the least one loudspeaker of the anti-sound system during the operation with the control signal based on a mathematical model of a thermal behavior of the loudspeaker and an expected mechanical load of the at least one loudspeaker of the anti-sound system during the operation with the control signal based on a mathematical model of a mechanical behavior the loudspeaker;

comparing the calculated expected thermal load or calculated expected mechanical load with a specified maximum load;

operating the loudspeaker with the control signal, if the expected calculated thermal load or the calculated expected mechanical load is smaller than or equal to the maximum load; and changing a spectrum of the control signal to obtain a corrected control signal if the calculated thermal load or the calculated mechanical load is greater than the maximum load, and operating the loudspeaker with the corrected control signal.

22. A motorized vehicle comprising:

a combustion engine;

an exhaust system, which is in fluid connection with the combustion engine; and an anti-sound system for the exhaust system, the anti-sound system comprising:

an anti-sound control unit;

a loudspeaker operatively connected to the anti-sound control unit for the reception of control signals, wherein the loudspeaker is adapted for generating an anti-sound in a sound generator which can be placed in a fluid connection with the exhaust system, wherein the generation of anti-sound by the loudspeaker is dependant upon a control signal received by the loudspeaker from the anti-sound control unit; and an error microphone operatively connected with the anti-sound control unit and arranged in a position of the exhaust system with reference to exhaust gas flow situated in the vicinity of the fluid connection between the sound generator and the exhaust system, wherein the error microphone is adapted to measure sound within the exhaust system, and to provide a corresponding output measuring signal to the anti-sound control unit;

wherein the anti-sound control unit is adapted to execute the steps of:

measuring sound inside the exhaust system;

calculating a control signal based on the measured sound;

calculating at least one of an expected thermal load of the least one loudspeaker of the anti-sound system during the operation with the control signal based on a mathematical model of a thermal behavior of the loudspeaker and an expected mechanical load of the at least one loudspeaker of the anti-sound system during the operation with the control signal based on a mathematical model of a mechanical behavior the loudspeaker;

comparing the calculated expected thermal load or calculated expected mechanical load with a specified maximum load;

operating the loudspeaker with the control signal, if the expected calculated thermal load or the calculated expected mechanical load is smaller than or equal to the maximum load; and changing a spectrum of the control signal to obtain a corrected control signal if the calculated thermal load or the calculated mechanical load is greater than the maximum load, and operating the loudspeaker with the corrected control signal.

* * * * *